(12) United States Patent
Furuta et al.

(10) Patent No.: US 8,230,734 B2
(45) Date of Patent: Jul. 31, 2012

(54) LEAF SPRING LOAD MEASURING DEVICE AND PROGRAM

(75) Inventors: Eijiro Furuta, Komagane (JP); Koichi Fukushima, Komagane (JP)

(73) Assignee: NHK Spring Co., Ltd., Yokohama-shi (JP)

( * ) Notice: Subject to any disclaimer, the term of this patent is extended or adjusted under 35 U.S.C. 154(b) by 478 days.

(21) Appl. No.: 12/575,355

(22) Filed: Oct. 7, 2009

(65) Prior Publication Data

US 2010/0018307 A1    Jan. 28, 2010

Related U.S. Application Data

(62) Division of application No. 11/520,553, filed on Sep. 13, 2006, now Pat. No. 7,624,631.

(30) Foreign Application Priority Data

Sep. 15, 2005    (JP) .................................. 2005-268630

(51) Int. Cl.
    *G01L 1/04*    (2006.01)
(52) U.S. Cl. ......................................................... 73/161
(58) Field of Classification Search ...................... 73/161
    See application file for complete search history.

(56) References Cited

U.S. PATENT DOCUMENTS

| | | | |
|---|---|---|---|
| 2,784,588 A | 3/1957 | Humble et al. | |
| 3,897,844 A | 8/1975 | Chevalier | |
| 5,088,333 A | 2/1992 | Kiely et al. | |
| 5,291,360 A | 3/1994 | Foote | |
| 6,199,427 B1 | 3/2001 | Kroll et al. | |
| 7,069,777 B2 | 7/2006 | Umebayashi | |
| 7,143,643 B2 | 12/2006 | Umebayashi | |
| 7,327,536 B2 * | 2/2008 | Wada et al. | ................ 360/244.5 |

FOREIGN PATENT DOCUMENTS

| | | |
|---|---|---|
| JP | 08-247911 A | 9/1996 |
| JP | 10-055634 A | 2/1998 |
| JP | 2001-091424 A | 4/2001 |
| JP | 2004-355678 A | 12/2004 |

OTHER PUBLICATIONS

Japanese Office Action dated Jun. 8, 2010 and English translation thereof, issued in counterpart Japanese Application No. 2005-268630.

* cited by examiner

*Primary Examiner* — Lisa Caputo
*Assistant Examiner* — Octavia D Davis-Hollington
(74) *Attorney, Agent, or Firm* — Holtz, Holtz, Goodman & Chick, PC

(57) ABSTRACT

A leaf spring load measuring device of the present invention comprises a weighing mechanism, a measuring mechanism, a metering mechanism, and a control mechanism. The weighing mechanism applies a load heavier than a working load to a leaf spring, thereby bending the leaf spring in its thickness direction, and maintains the resulting state for a predetermined hold time. The measuring mechanism measures a load value of the leaf spring in a manner such that the spring is subjected to a load within a range of the working load. The metering mechanism meters a displacement of the spring when the load value is measured. The control mechanism controls the weighing mechanism, the metering mechanism, and the measuring mechanism, and has a timer function to meter the hold time.

3 Claims, 12 Drawing Sheets

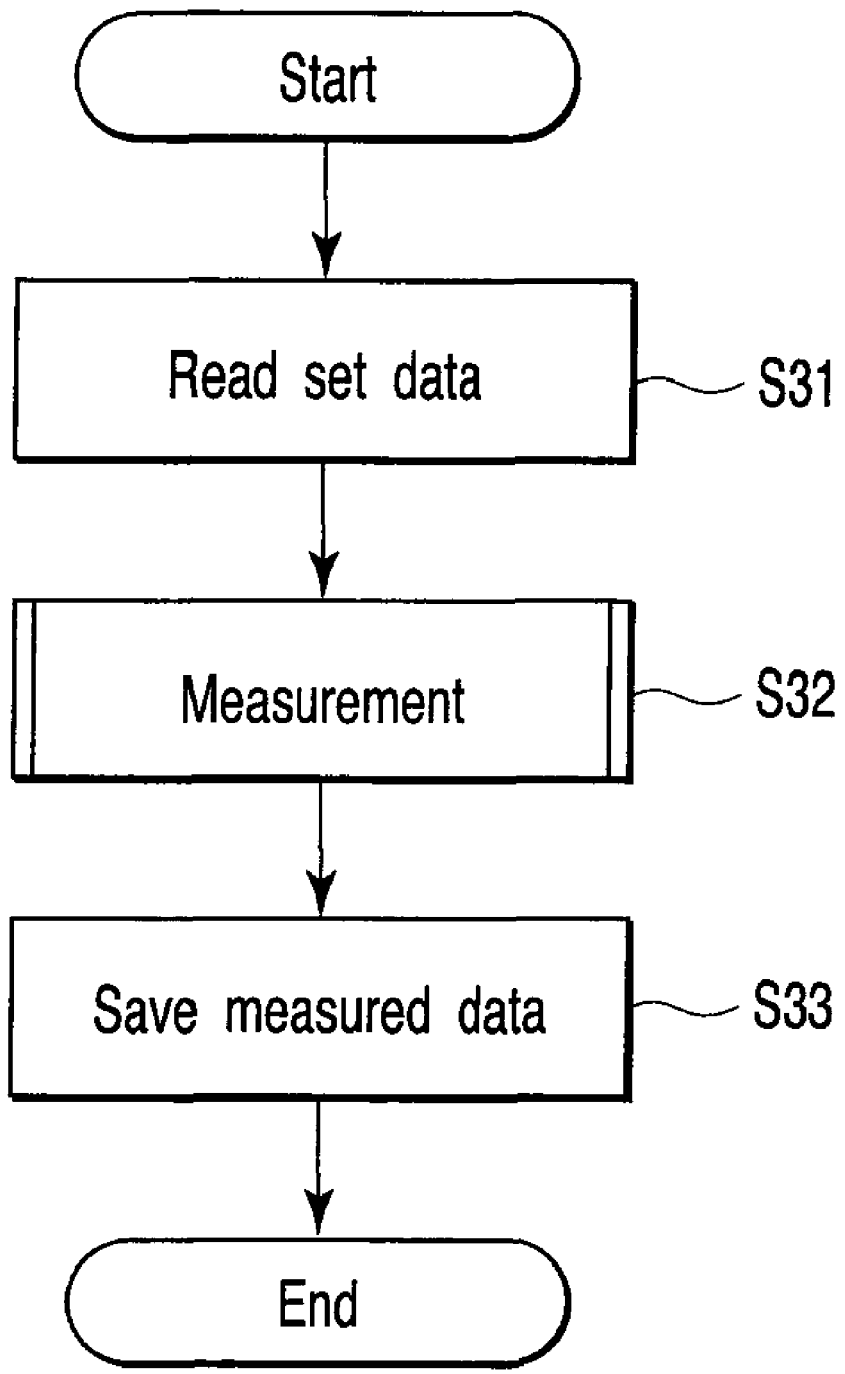
F I G. 14

LEAF SPRING LOAD MEASURING DEVICE AND PROGRAM

CROSS-REFERENCE TO RELATED APPLICATIONS

The present application is a Divisional Application of U.S. application Ser. No. 11/520,553 filed Sep. 13, 2006 now U.S. Pat. No. 7,624,631, which is based upon and claims the benefit of priority from prior Japanese Patent Application No. 2005-268630, filed Sep. 15, 2005, the entire contents of which are incorporated herein by reference.

BACKGROUND OF THE INVENTION

1. Field of the Invention

The present invention relates to a leaf spring load measuring device and a program for evaluating the sag resistance of a leaf spring.

2. Description of the Related Art

A generally known hard disc drive contains therein a magnetic disc, a magnetic head for writing information to and reading it from the disc, and a leaf spring called a suspension that supports the head on its distal end. The spring is bent toward the disc and presses the head against the disc. When the disc rotates, the head and the spring float under the influence of an airflow that is generated above the surface of the disc. In this floating state, the head can write information to or read it from the disc.

Nowadays, with the recording densities of magnetic discs being improved drastically, setting the load of the leaf spring that has the aforesaid function requires very high precision. Therefore, a high-precision load measuring device is used to measure the load of the leaf spring. The load measuring device comprises a clamper that supports the leaf spring, a load cell that causes a probe to abut against the spring, and a lift mechanism that raises and lowers the load cell.

In the load measuring device of this type, as described in Jpn. Pat. Appln. KOKAI Publication No. 2004-355678, for example, the load cell is lowered toward the load value to measure the load of the spring. If the measurement result is different from a standard one, the load is corrected by applying, for example, a laser beam.

In recent years, PCs and their peripheral devices are expected to have high resistance against shock, and so are hard disc drives. Thus, if a magnetic head is in contact with a magnetic disc when a heavy shock acts on a hard disc drive that uses a leaf spring, the spring may possibly warp and sag. In the case of a leaf spring whose load is corrected by a laser beam, in particular, residual stress in the spring is removed by the laser beam. It is necessary, therefore, to check and see whether the leaf spring with the corrected load is equivalent in sag resistance to one with its load uncorrected. This check requires a test for evaluating the sag resistance of the corrected leaf spring. However, the conventional load measuring device cannot deal with the evaluation of the sag resistance and needs some improvement.

BRIEF SUMMARY OF THE INVENTION

An object of the present invention is to provide a leaf spring load measuring device capable of accurately evaluating sag of leaf springs and supplying leaf springs with sag resistance.

Another object of the invention is to provide a program capable of accurately evaluating sag of leaf springs and supplying leaf springs with sag resistance.

In order to achieve the above objects, a load measuring device according to an aspect of the invention comprises a weighing mechanism which applies a load heavier than a working load to a leaf spring, thereby bending the leaf spring in a thickness direction thereof, and maintains the resulting state for a predetermined hold time, a measuring mechanism which measures a load value of the leaf spring in a manner such that the leaf spring is subjected to a load within a range of the working load, a metering mechanism which meters a displacement of the leaf spring when the load value is measured, and a control mechanism which controls the weighing mechanism, the metering mechanism, and the measuring mechanism.

For example, the leaf spring is a suspension which supports a head of a hard disc drive. Preferably, in this case, the hold time is set to 7 seconds or more.

In order to achieve the above objects, a program according to another aspect of the invention is a program readable by a computer connected to a weighing mechanism which applies a load to a leaf spring, a measuring mechanism which measures a value of the load applied by the weighing mechanism, a metering mechanism which meters a displacement of the leaf spring when the load is applied by the weighing mechanism, and a display mechanism on which an operation screen is displayed, the program making the computer execute process routines of applying, by the weighing mechanism, a load heavier than a working load to the leaf spring, thereby bending the leaf spring in a thickness direction thereof, maintaining, for a predetermined hold time, the state in which the load heavier than the working load is applied to the leaf spring by the weighing mechanism, applying a load within a range of the working load to the leaf spring by the weighing mechanism and acquiring a load value then measured by the measuring mechanism and a displacement value then metered by the metering mechanism, storing the measured load value and the metered displacement value in a memory section of the computer on a time-series basis, and displaying the measured load value and the metered displacement value on the operation screen.

According to the present invention, there may be provided a leaf spring load measuring device of which the degree of sag of a leaf spring can be evaluated accurately and efficiently without regard to an operator's skill or experience.

Additional objects and additional advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 14 is a flowchart showing measurement of second and subsequent load values based on an evaluation method using the load measuring device shown in FIG. 1.

DETAILED DESCRIPTION OF THE INVENTION

An embodiment of a leaf spring load measuring device to which a program of the present invention is applied will now be described with reference to FIGS. 1 to 14.

Figure 1:
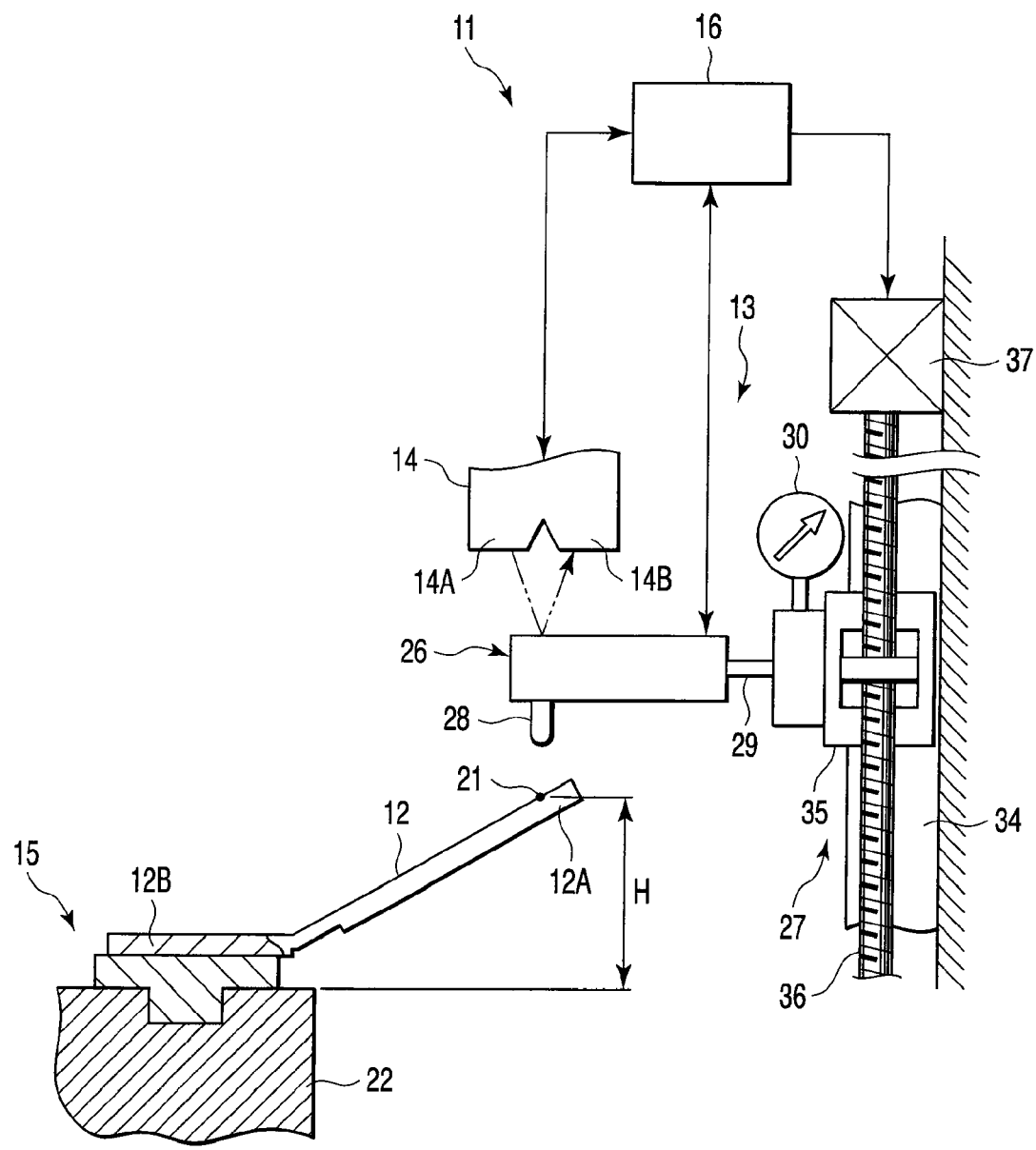
FIG. 1 is a sectional view showing a leaf spring load measuring device according to an embodiment of the invention.

As shown in FIG. 1, a load measuring device 11 comprises a measuring mechanism 13 for measuring a load of a leaf spring 12, a metering mechanism 14 for metering a displacement of the spring 12, a clamp mechanism 15 for fixedly supporting the spring 12, and a control mechanism 16 for controlling these elements. The leaf spring 12 is fixed to the clamp mechanism 15. The spring 12 is formed of a suspension that supports a magnetic head of a hard disc drive. The spring 12 is bent in a direction in which the magnetic head is mounted. A load point 21 at which a load value is measured by the measuring mechanism 13 is provided near a distal end 12A of the leaf spring 12.

The clamp mechanism 15 has a base 22 and a clamping cylinder (not shown) that is located opposite the base 22 with the leaf spring 12 between them. The spring 12 is held between the base 22 and the clamping cylinder, whereby its proximal end 12B is fixed.

The measuring mechanism 13 comprises, for example, a load cell 26 for measuring a load of the leaf spring 12 and a lift mechanism 27 that supports the load cell 26 for up-and-down motion. The load cell 26 comprises a probe 28 that abuts against the spring 12, a strain gauge 29 to which the probe 28 is fixed, and a load indicator 30 fixed to the strain gauge 29. The load of the leaf spring 12 can be noticed by visual observation on the indicator 30. The measuring mechanism 13 transmits the load value measured by the strain gauge 29 to the control mechanism 16. Although the measuring mechanism 13 is partially composed of a load cell 26 according to the present embodiment, it may alternatively be formed of any other load sensor, such as a piezoelectric load sensor.

The lift mechanism 27 comprises, for example, a linear guide 34, a slider 35 that slides on the linear guide 34, a ball screw 36 for driving the slider 35 for up-and-down motion, and a stepping motor 37 for driving the screw 36. If the stepping motor 37 is driven under the control of the control mechanism 16, the ball screw 36 rotates to cause the slider 35 to move up and down along the linear guide 34. As the slider 35 moves up and down, so does the load cell 26. Alternatively, the lift mechanism 27 may be composed of an air cylinder or the like. In the present embodiment, the measuring mechanism 13 serves to apply a load that exceeds a working load to the leaf spring 12, so that it is also equivalent to a weighing mechanism according to the present invention.

The metering mechanism 14 is formed of a laser displacement sensor, for example. The metering mechanism 14 has a transmitter element 14A that transmits a laser beam and a receiver element 14B that receives the laser beam from the transmitter element 14A. The metering mechanism 14 transmits the laser beam from the transmitter element 14A toward the upper surface of the load cell 26, and receives the laser beam reflected by the upper surface of the load cell 26 by means of the receiver element 14B, thereby measuring a distance from the measuring mechanism 13. Thereupon, the displacement of the leaf spring 12 is measured. The metering mechanism 14 transmits data on the measured value of displacement of the spring 12 to the control mechanism 16.

Figure 2:
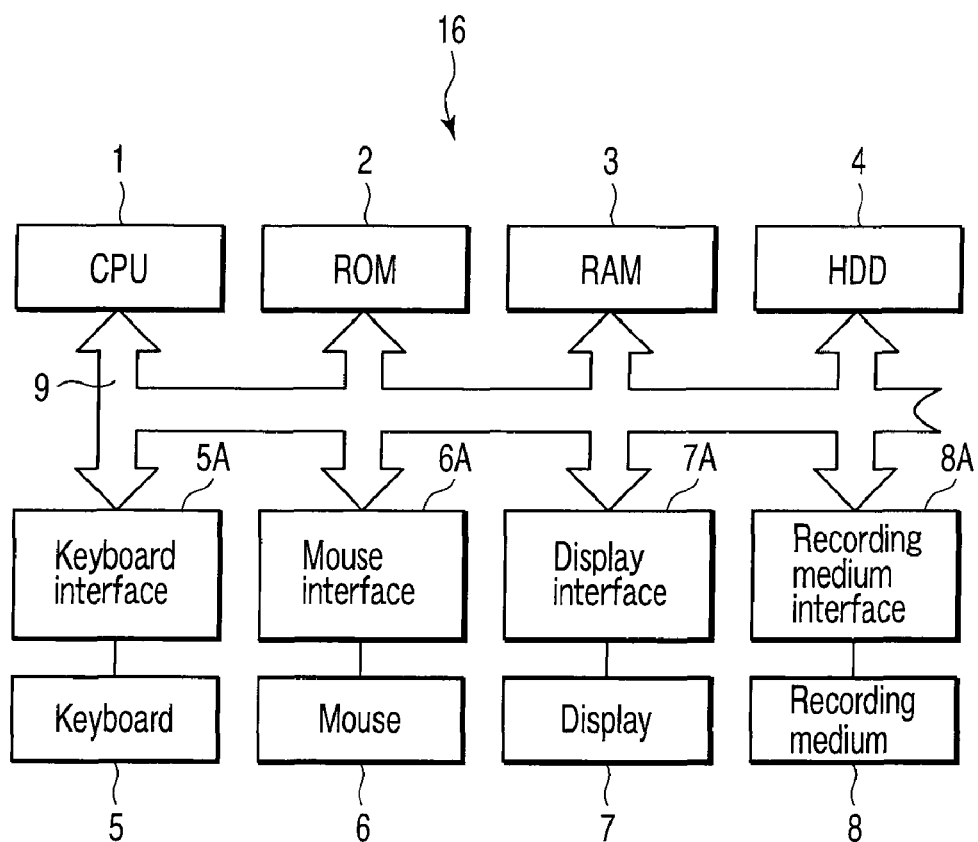
FIG. 2 is a block diagram showing a principal hardware configuration of a computer that constitutes a control mechanism of the load measuring device shown in FIG. 1.

As shown in FIG. 2, a computer that constitutes the control mechanism 16 comprises a central processing unit (CPU) 1, read-only memory (ROM) 2, random access memory (RAM) 3, hard disc drive (HDD) unit 4, and various input/output interfaces. The ROM 2 and the RAM 3 constitute a main memory section. The HDD unit 4 constitutes an auxiliary memory unit. The interfaces include a keyboard interface 5A, mouse interface 6A, display interface 7A, recording medium interface 8A, etc. The CPU 1 is connected to the ROM 2, RAM 3, HDD unit 4, and interfaces 5A, 6A, 7A and 8A by a bus line 9, such as an address bus, data bus, etc. The RAM 3 is equivalent to a memory section according to the present invention.

The control mechanism 16 has a plurality of drivers (not shown) and an input/output controller that connects the drivers and the bus line 9. The drivers correspond to the load cell 26, metering mechanism 14, stepping motor 37 of the lift mechanism 27, and clamping cylinder, individually. The control mechanism 16 controls the drive of the load cell 26, metering mechanism 14, stepping motor 37 of the lift mechanism 27, and clamping cylinder through the input/output controller and the drivers.

The keyboard interface 5A is connected to a keyboard 5 that is provided with character keys, numeric keys, a space key, an enter key, cursor keys, function keys, etc. The display interface 7A is connected to a display unit 7 for use as a display mechanism. The display unit 7 is composed of, for example, a liquid crystal display, a CRT display, etc. The mouse interface 6A is connected to a mouse 6 for use as a pointing device that moves a pointer displayed on a screen of the display unit 7. The recording medium interface 8A is connected to a recording medium 8, such as a floppy disc, CD-ROM, etc.

The HDD unit 4 is loaded with a two-point measurement program, which is dedicated software for the load measuring device 11, a backbend program, and a manual operation program. Although these programs are loaded into the HDD unit 4, they may alternatively be read from the recording medium 8 in which they are stored in advance, for example.

Figure 3:
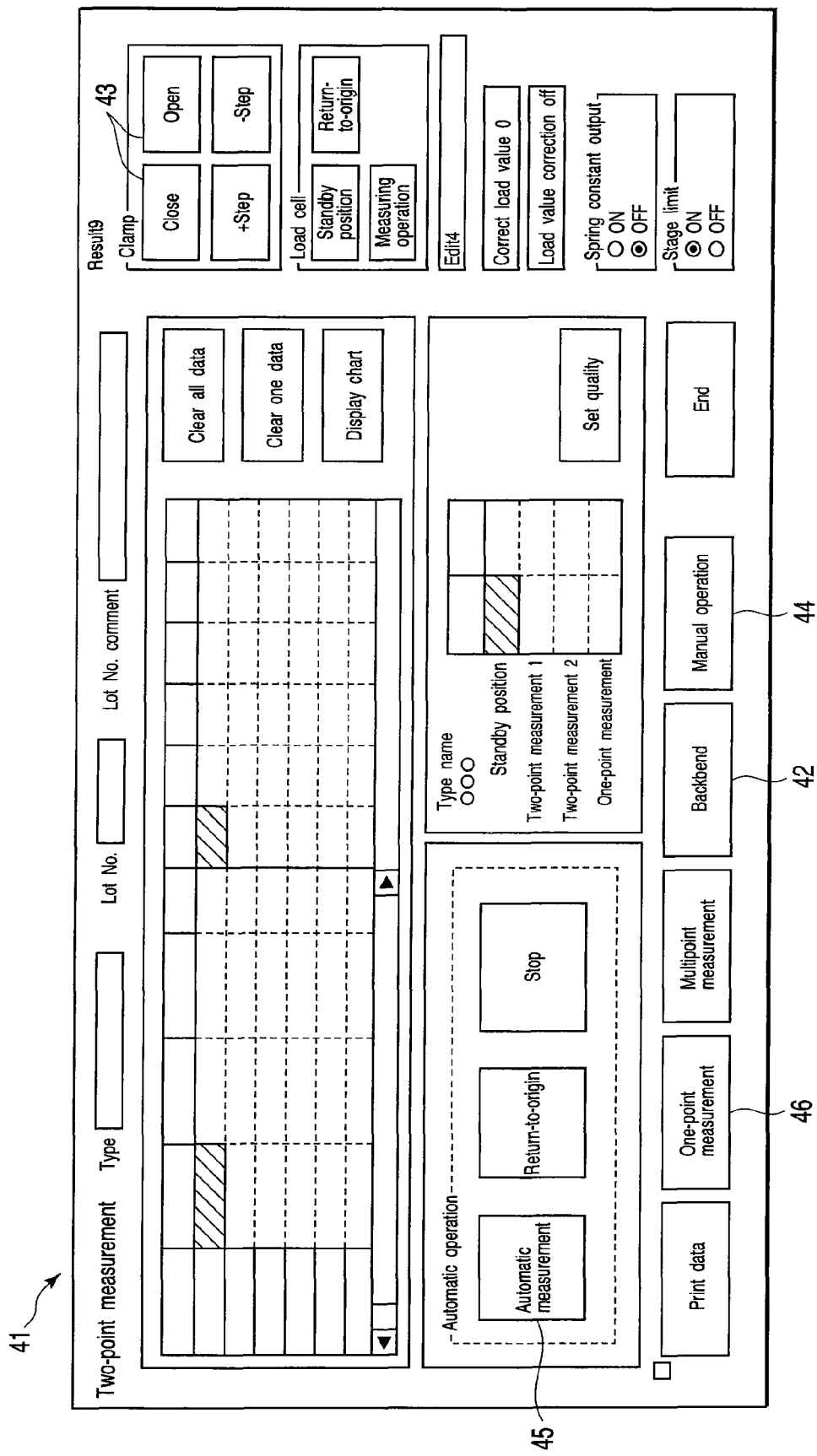
FIG. 3 is a diagram showing a two-point measurement screen displayed on the control mechanism of the load measuring device shown in FIG. 1.
Figure 4:
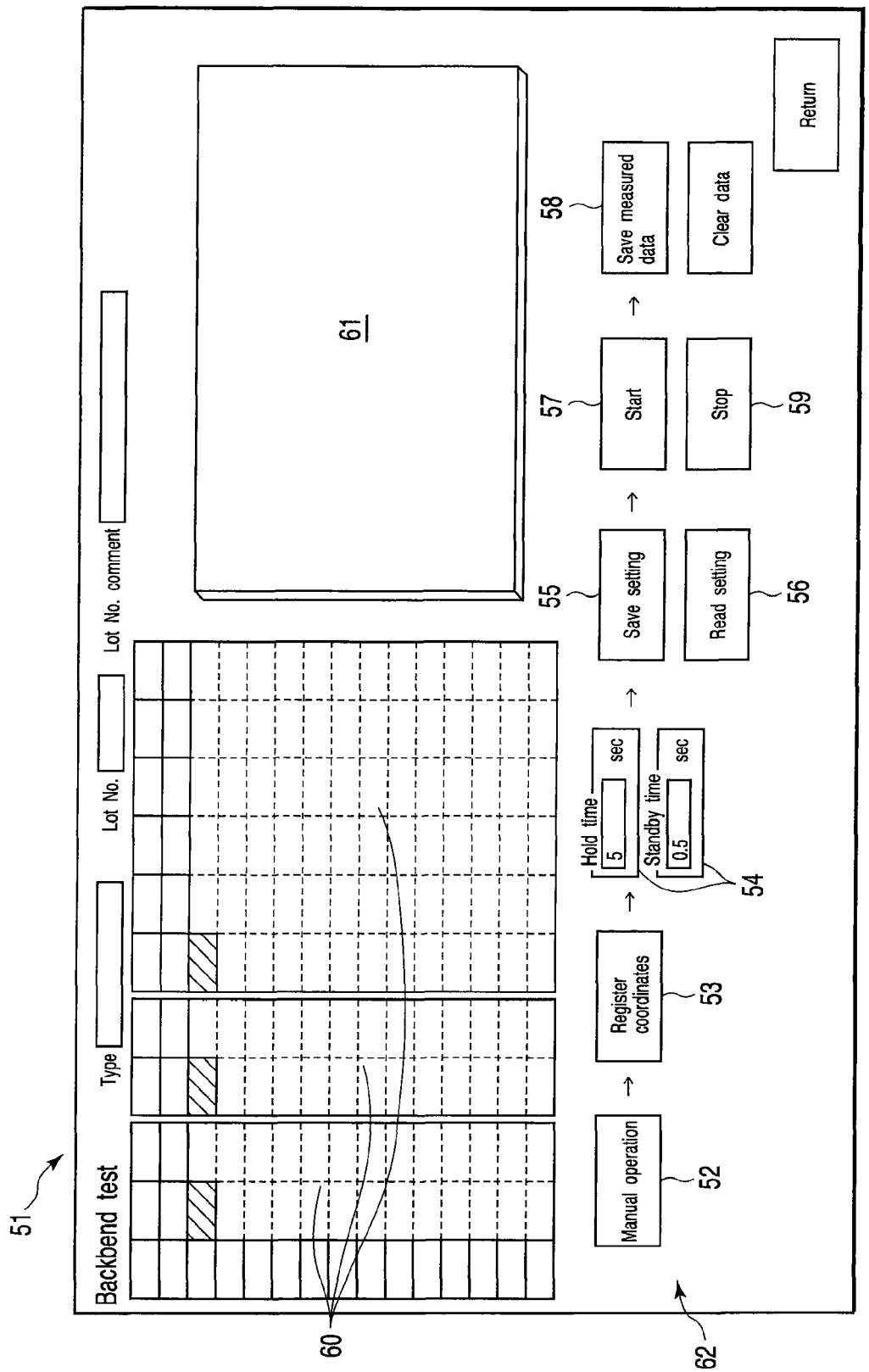
FIG. 4 is a diagram showing a backbend test screen displayed on the control mechanism.

An operation screen displayed on the display unit 7 of the control mechanism 16 will now be described with reference to FIGS. 3 to 5. A two-point measurement screen 41 shown in FIG. 3 is a screen that is displayed when the two-point measurement program of the load measuring device 11 is started. The two-point measurement screen 41 is provided with a backbend button 42, switch buttons 43 for the clamping cylinder, a manual operation button 44, an automatic measurement button 45, and a one-point measurement button 46. The backbend button 42 is used to execute a backbend test for evaluating sag of the leaf spring 12. If the backbend button 42 is selected, the backbend program is activated on the control mechanism 16, whereupon a backbend test screen 51 shown in FIG. 4 is displayed. If the automatic measurement button 45 is clicked, automatic measurement of a specific load value is started based on regular two-point measurement that is different from the backbend test. The two-point measurement program, the backbend program, and the manual operation program are programs that can be read by the computer for the control mechanism 16, and are equivalent to programs according to the present invention.

As shown in FIG. 4, the backbend test screen 51 as an operation screen is provided with a numerical display area 60, a graph display area 61, and a button location area 62. The button location area 62 is provided with a manual operation button 52, coordinate register button 53, entry columns 54 for hold time and standby time, setting save button 55, setting read button 56, start button 57, measured data save button 58, stop button 59, etc. The buttons 52 to 59 are arranged from left to right in the button location area 62 shown in FIG. 4, in the order based on the procedure of the backbend test in which the load value is measured.

Figure 5:
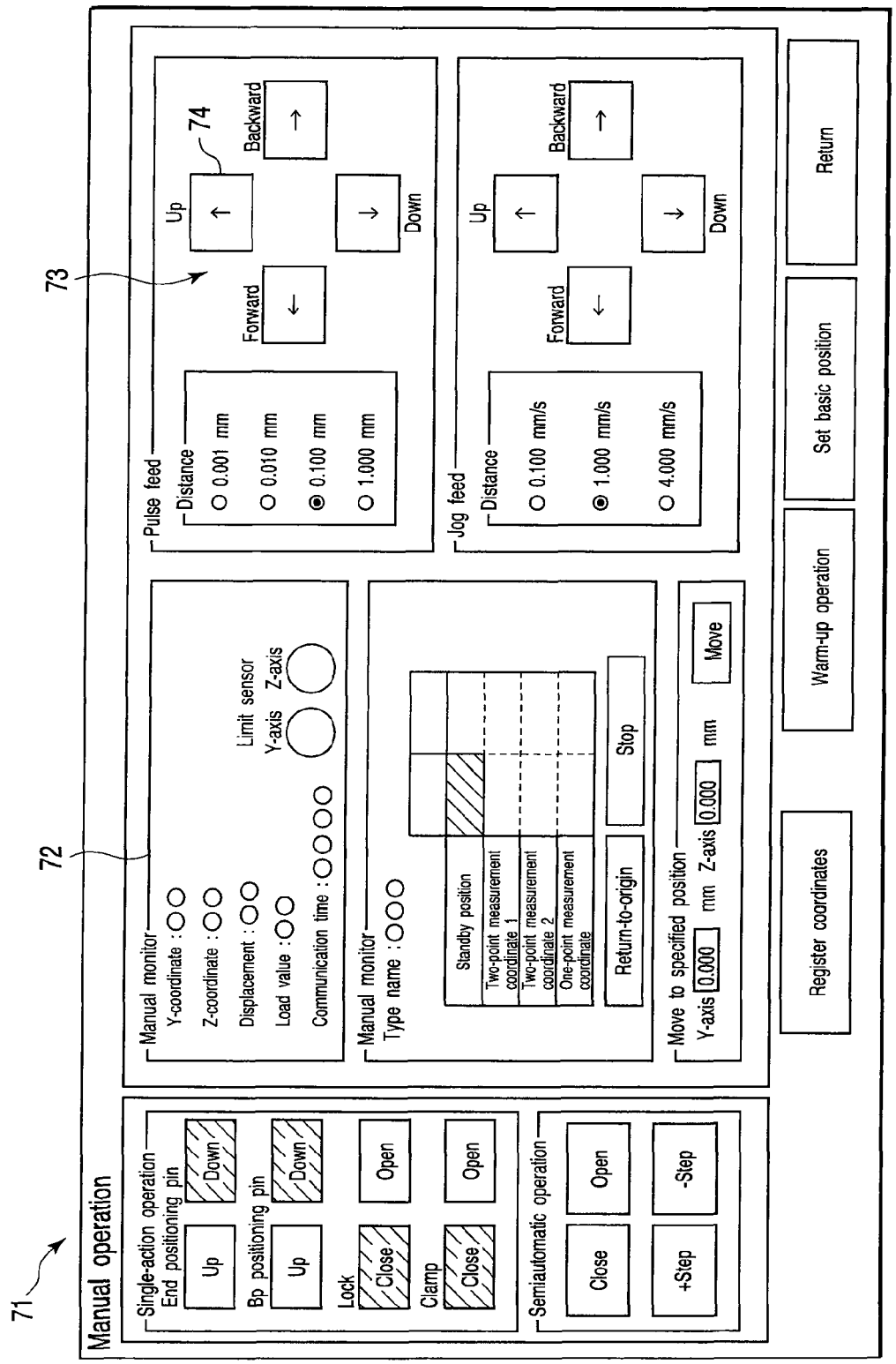
FIG. 5 is a diagram showing a manual operation screen displayed on the control mechanism.

If the manual operation button 44 is clicked, the manual operation program is activated on the control mechanism 16, and a manual operation screen 71 shown in FIG. 5 is displayed. The stop button 59 serves to stop the load measurement at any desired time.

The displacement of the leaf spring 12, the load value of the spring 12 for this displacement, the coordinates of the measuring mechanism 13, etc., are displayed in the numerical display area 60 on a time-series basis. The data displayed in the numerical display area 60 can be processed by using general-purpose spread sheet software. Graphs that indicate the degree of fluctuation of the specific load value and the like are displayed in the graph display area 61 on a time-series basis. The specific load value of the spring 12 and the like can be recognized through the numerical display area 60 and the graph display area 61 at any time during measurement. If desired numerical values are entered in the entry columns 54 for hold time and standby time, the time during which the measuring mechanism 13 applies the load on the spring 12 can be selected freely. Thus, the control mechanism 16 has a timer function to measure the time during which the measuring mechanism 13 applies the load to the spring 12.

As shown in FIG. 5, the manual operation screen 71 is provided with a display column 72 in which the measured displacement, load value, etc., of the leaf spring 12 are displayed, pulse feed buttons 73 for manually moving the load cell 26 for an infinitesimal distance, and the like. A movement distance that can be covered by one click of any of the pulse feed buttons 73 can be freely selected among 0.001, 0.01, 0.1, and 1 mm.

A flow of the backbend test for evaluating the sag resistance of the leaf spring 12 will now be described with reference to FIG. 1 and FIGS. 6 to 9.

Figure 6:
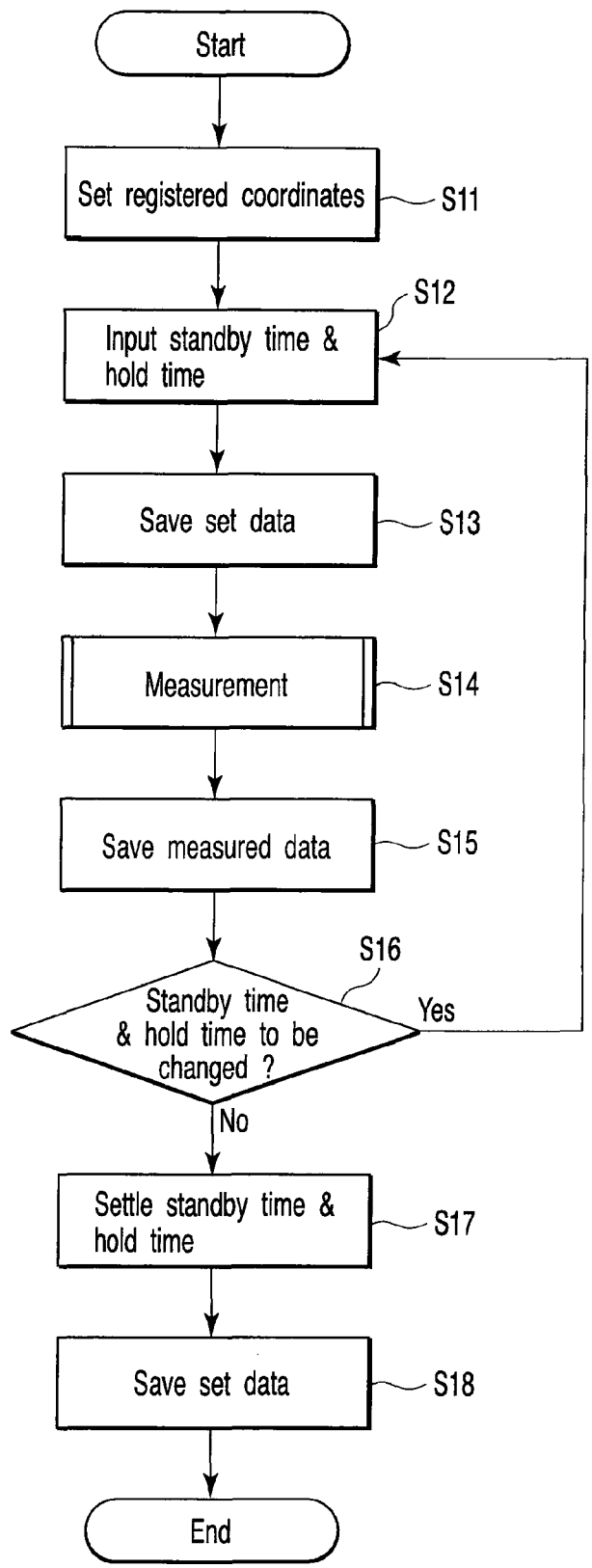
FIG. 6 is a flowchart showing individual processes of a backbend test using the load measuring device shown in FIG. 1.

FIG. 6 is a flowchart showing an outline of the backbend test. Before registered coordinate setting in Step S11 shown in FIG. 6, the two-point measurement program is started in advance in the control mechanism 16. When the two-point measurement program is started, the two-point measurement screen 41 shown in FIG. 3 is displayed on the display unit 7 of the control mechanism 16. If the backbend button 42 of the two-point measurement screen 41 is clicked, the backbend program is started, whereupon the backbend test screen 51 shown in FIG. 4 is activated.

In Step S11 shown in FIG. 6, the coordinate register button 53 is clicked on the backbend test screen 51 to set registered coordinates. In setting the registered coordinates, the position of the probe 28 is controlled to register loaded positions and the values of loads applied to the leaf spring 12. The registered loaded positions are stored into the RAM 3 as the memory section. In Step S11, the computer that constitutes the control mechanism 16 is caused to execute the following process routines, that is, to make the operation screen accept registration of applied load values that exceed the working load of the leaf spring 12 and make the RAM 3 of the computer store the applied load values registered through the operation screen. Although this setting of the registered coordinates is performed by an operator who accepts entry of the loaded positions, it may alternatively be carried out automatically by the control mechanism 16.

After the registered coordinate setting, the leaf spring 12 that is used for the registered coordinate setting is removed, and another leaf spring 12 to be an object of measurement is fixed to the clamp mechanism 15. Then, a standby time and a hold time are input in Step S12 of FIG. 6. The input standby time and hold time are stored into the RAM 3 of the control mechanism 16, for example. In this case, the standby time is a predetermined time for a standby to provide for subsequent load measurement after the application of the load. The hold time defines a time during which the load is applied to the leaf spring 12.

The standby time and the hold time are input individually to the entry columns 54 for hold time and standby time of the backbend test screen 51 shown in FIG. 4. The standby time and the hold time input in this case are 0.5 and 5 seconds, respectively, for example. In Step S12, the computer that constitutes the control mechanism 16 is caused to execute the following process routines, that is, to make the operation screen accept entry of the hold time and make the RAM 3 of the computer store the hold time input through the operation screen. The standby time and the hold time are not limited to those values but may be set freely.

Figure 7:
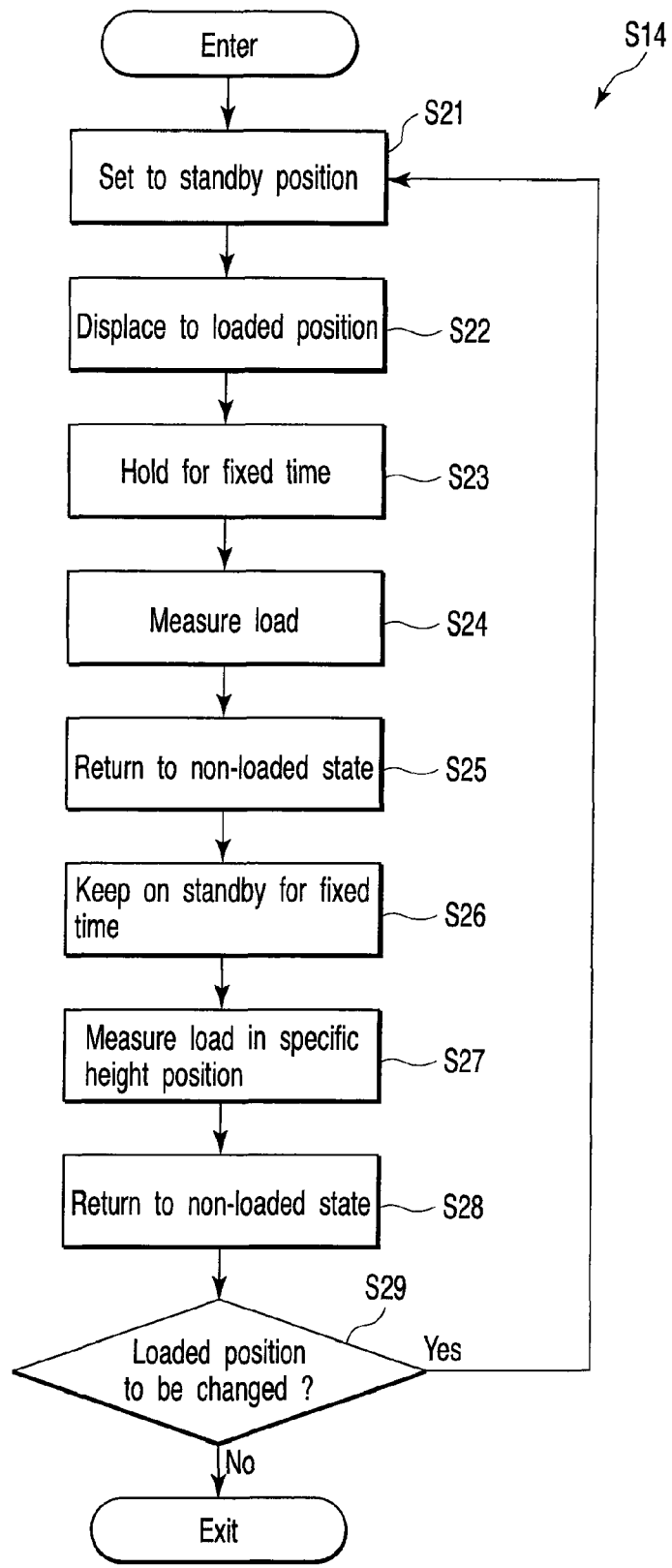
FIG. 7 is a flowchart showing details of measurement steps of the backbend test.

After those parameters are input, the set data are saved in Step S13 of FIG. 6. The set data are saved by clicking the setting save button 55 shown in FIG. 4. In Step S14, the load of the leaf spring 12 is measured. The load measurement involves further detailed processes, as shown in FIG. 7. Thus, this measurement will now be described in order with reference to the processes of FIG. 7.

If the start button 57 of the backbend test screen 51 shown in FIG. 4 is clicked, the steps of FIG. 7 automatically proceed under the control of the control mechanism 16. First, in Step S21 of FIG. 7, the measuring mechanism 13 is set in its standby position. In this case, the load point 21 that is situated near the distal end 12A of the leaf spring 12 is in a position corresponding to a height H at which no load is applied. In each of the following processes for measuring the load of the spring 12, the probe 28 of the measuring mechanism 13 is caused to abut against the load point 21. While the measuring mechanism 13 in the standby position and the spring 12 are in the state shown in FIG. 1, the spring 12 may possibly be subjected to some load only if it is in a position such that it receives a lighter load than in a specific height position for the measurement of the specific load value.

Figure 8:
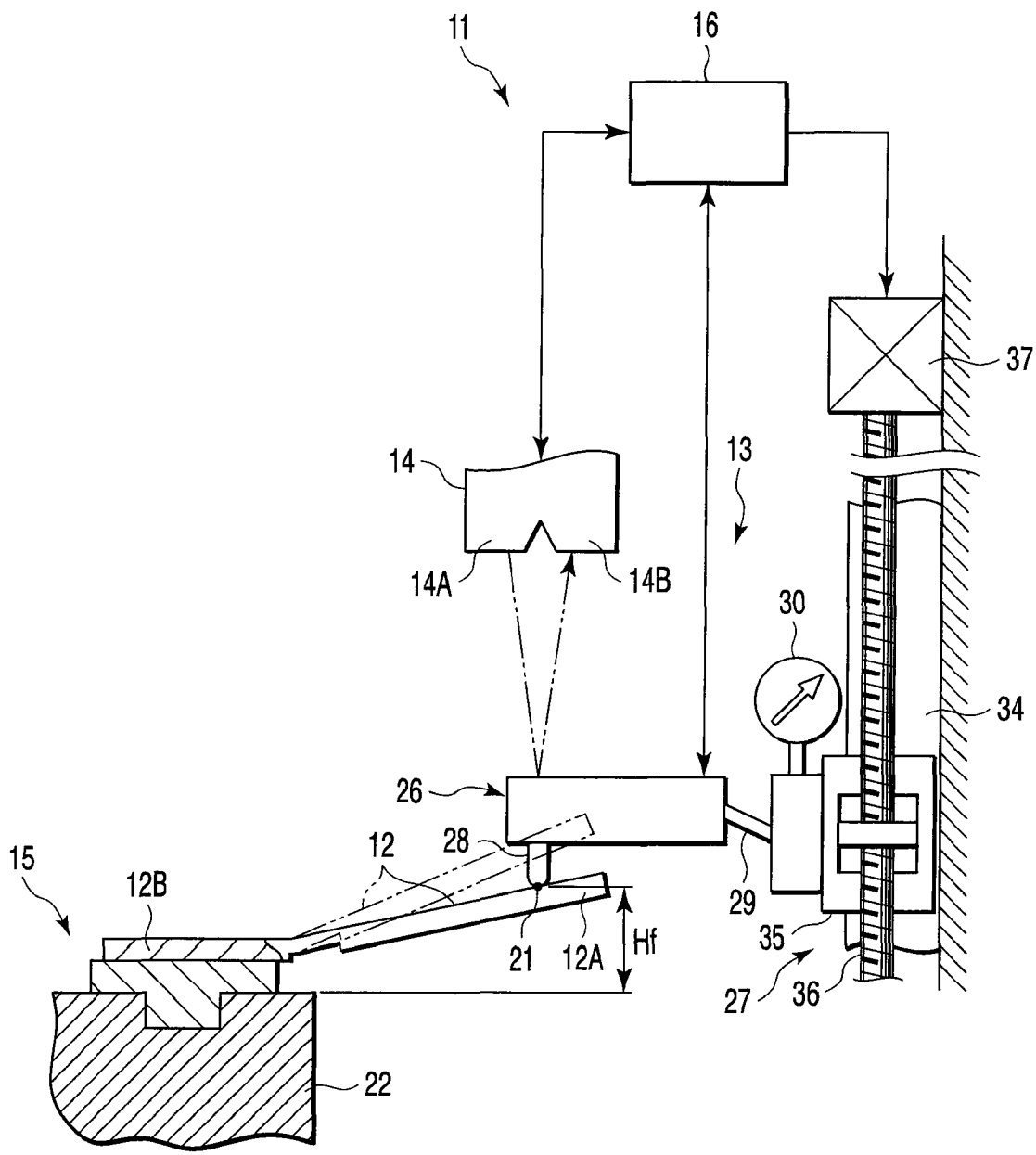
FIG. 8 is a sectional view showing a state in which the load measuring device shown in FIG. 1 applies a load to a leaf spring.

In Step S22 of FIG. 7, the measuring mechanism 13 is lowered to displace the leaf spring 12 to a loaded position such that a load heavier than the working load is applied to the spring 12. The spring 12 bends in its thickness direction and takes a loaded state, as shown in FIG. 8. In this loaded state, the spring 12 is sagged. In this case, the load point 21 of the spring 12 is situated at a height Hf that is lower than the non-loaded height H. In Step S22, the computer that constitutes the control mechanism 16 is caused to execute a process routine such that the leaf spring 12 is bent by applying a load higher than the working load to the spring 12 by the measuring mechanism 13.

In Step S23, the leaf spring 12 is kept in the loaded state for a predetermined hold time. In the case of the aforesaid setting, the hold time is 5 seconds. In Step S23, the computer that constitutes the control mechanism 16 is caused to execute a process routine such that the spring 12 is kept subjected to a load higher than the working load for a predetermined hold time by the measuring mechanism 13.

In Step S24 of FIG. 7, the load indicated by the load cell 26 is measured. Although this measured value serves as a standard of the load for the loaded state, it may be measured in Step S27 without being measured in this stage.

In Step S25 of FIG. 7, the leaf spring 12 is restored to a non-loaded state, as shown in FIG. 1. Then, in Step S26 of FIG. 7, the spring 12 is kept on standby for a fixed time, e.g., 0.5 seconds for the case of the aforesaid setting.

Figure 9:
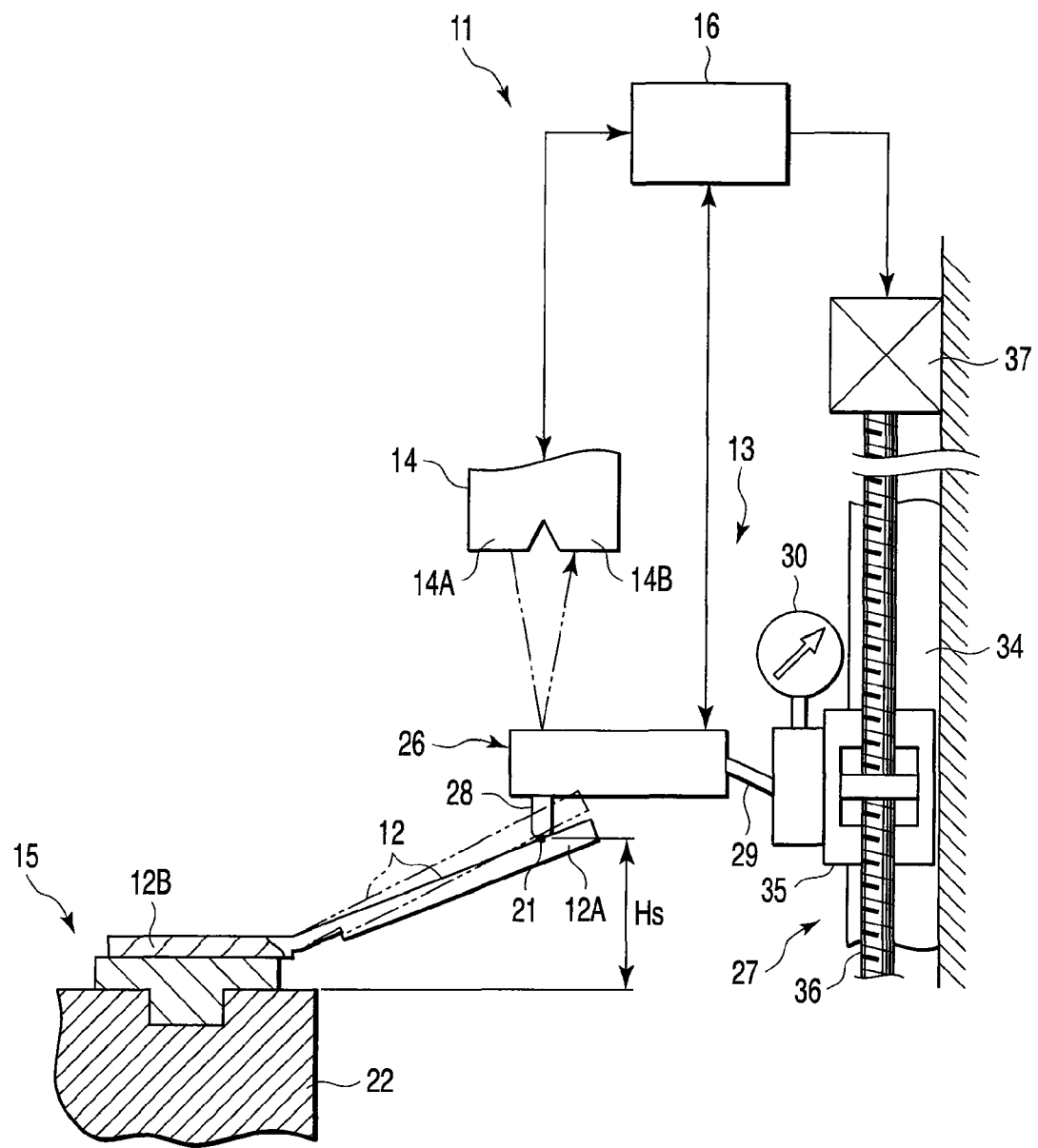
FIG. 9 is a sectional view showing a state in which the load measuring device shown in FIG. 1 measures a specific load value of the leaf spring.

In Step S27, the specific load value for the specific height position is measured. As shown in FIG. 9, the specific load value of the leaf spring 12 is measured with the spring 12 subjected to a load within the range of the working load. In this case, the load point 21 of the spring 12 is situated at a height position Hs higher than the loaded height position Hf and lower than the non-loaded height position H. As the specific load value is measured, the displacement of the leaf spring 12 is metered by the metering mechanism 14. In Step S27, the computer that constitutes the control mechanism 16 is caused to execute a process routine such that the spring 12 is subjected to a load within the range of the working load by the measuring mechanism 13 and the load value then measured by the measuring mechanism 13 and the displacement value metered by the metering mechanism 14 are acquired. The specific load value in this specific height position is measured based on two-point measurement.

The two-point measurement of the specific load value is made in a manner such that the load is measured in two displacement positions on either side of the specific height position for a target displacement of the leaf spring 12. In the two-point measurement, a spring constant of the spring 12 is calculated from load values and displacements at two spots. A target load value is calculated by multiplying this spring constant by the displacement for the specific height position. It is to be understood that the specific load value may be measured by one-point measurement such that the load value is measured only in a target specific height position. Since a distortion in the load cell 26 inevitably causes a measurement error in this two-point measurement, the actual displacement of the leaf spring 12 is metered by the metering mechanism 14 without being based on the rotational frequency of the ball screw 36 or the like.

After the measurement of the specific load value, the measuring mechanism 13 is raised to restore the leaf spring 12 to the non-loaded state in Step S28 of FIG. 7. In Step S29, the control mechanism 16 asks the operator to determine whether or not to measure the load of the spring 12 with the loaded position changed. If the operator decides to change the loaded position for the measurement, the load cell 26 is set in the standby position, and the load value is measured again. Normally, this load value measuring operation is repeated, for example, about 20 times with the loaded position changed.

The load value and the measured displacement obtained by the repeated measurement are stored into the RAM 3 of the control mechanism 16. Thus, the computer that constitutes the control mechanism 16 is caused to execute a process routine such that the measured load value and the measured displacement value are stored into the RAM 3 of the computer on a time-series basis. Further, the load value and the measured displacement value obtained by the repeated measurement are numerically displayed in the numerical display area 60 of the backbend test screen 51, which is the operation screen displayed on the display unit 7. Furthermore, the load value and the measured displacement value are graphically displayed in the graph display area 61 of the backbend test screen 51 on a time-series basis. In this manner, the computer that constitutes the control mechanism 16 is caused to execute a process routine such that the measured load value and the measured displacement value are displayed on the operation screen.

When the measurement of the load of the leaf spring 12 is finished, the measured data are saved in Step S15 of FIG. 6. The measured data are saved by clicking the measured data save button 58 shown in FIG. 4. In measuring the load with the standby time and the hold time changed, in Step S16, a standby time and a hold time are input anew, and the load value is measured again.

When the measurement is finished, the standby time and the hold time as conditions for the measurement are settled in Step S17 of FIG. 6. The set data including the settled conditions are saved in the control mechanism 16 in Step S18 of FIG. 6. When the set data are saved, the measurement process for the load value of the leaf spring 12 terminates. The measurement process for the load of the spring 12 can be interrupted at any time by clicking the stop button 59 shown in FIG. 4.

According to the present embodiment, the operator is expected to depress various buttons to check the processes shown in FIGS. 6 and 7 in the middle. Alternatively, however, the backbend program may be arranged so that the control mechanism 16 automatically makes measurement without asking the operator to make a decision in each process. Further, the registered coordinate setting in Step S11 mentioned before can be performed manually by utilizing the manual operation screen 71 as required, as well as automatically by means of the control mechanism 16. If the an ascent button 74 shown in FIG. 5 is clicked a plurality of times, in this case, for example, the load cell 26 ascends for a distance corresponding to the number of clicks.

Figure 10:
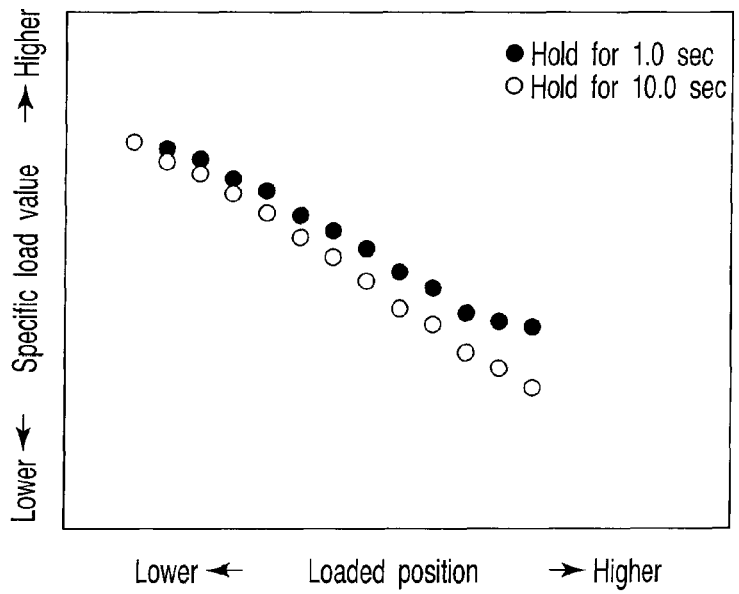
FIG. 10 is a graph showing how the degree of sag of the leaf spring varies depending on hold time.

FIG. 10 is a graph showing the relationship between the specific load value and the time during which the leaf spring 12 is kept loaded. In FIG. 10, each circle indicates a case where the loaded state is kept for 10 seconds, and each disc for 1 second. As shown in FIG. 10, both the circle and the disc indicate a tendency that the specific load value decreases as the loaded position is elevated, that is, as the applied load becomes heavier. FIG. 10 also shows that the specific load value is smaller when the hold time is 10 seconds than when the hold time is 1 second. This data indicates that the longer the hold time, the smaller the specific load value based on a given applied load is, that is, the more the leaf spring 12 sags.

Figure 11:
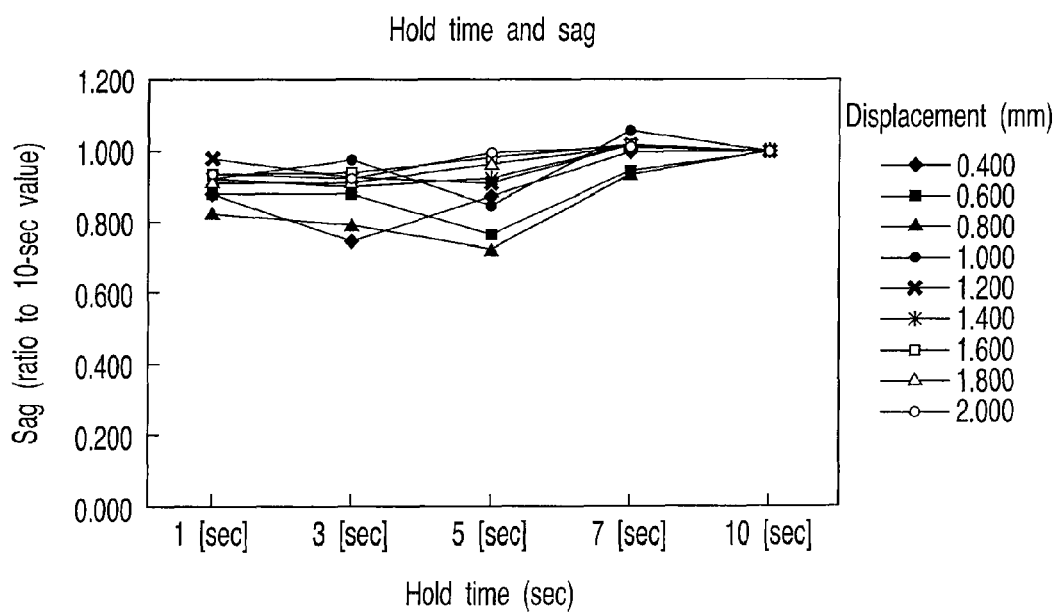
FIG. 11 is a graph showing the relationship between the degree of sag of the leaf spring and the hold time during which a loaded position is maintained.

FIG. 11 is a graph showing the relationship between the degree of sag of the leaf spring and the hold time during which the loaded position is maintained. In this case, the backbend or displacement of the leaf spring is varied from 0.400 to 2.000 mm, each times by 0.200 mm. The sag of the leaf spring 12 is measured with respect to these conditions. In FIG. 11, the ordinate and abscissa axes represent the sag indicative of the degree of sag of the leaf spring 12 and the hold time, respectively. The sag is the ratio of the load value of the spring 12 for each hold time to a specific load value gf that the sagged spring 12 has if held for 10 seconds.

As shown in FIG. 11, the sag greatly varies for leaf springs 12 with hold times of 1 second, 3 seconds, and 5 seconds. For a spring 12 with the hold time of 7 seconds, the sag varies little. Preferably, therefore, the hold time should be set to 7 seconds or more in the aforesaid backbend test. If the hold time is 7 seconds or more, the leaf spring 12 can be sagged somewhat uniformly without regard to the displacement.

Figure 12:
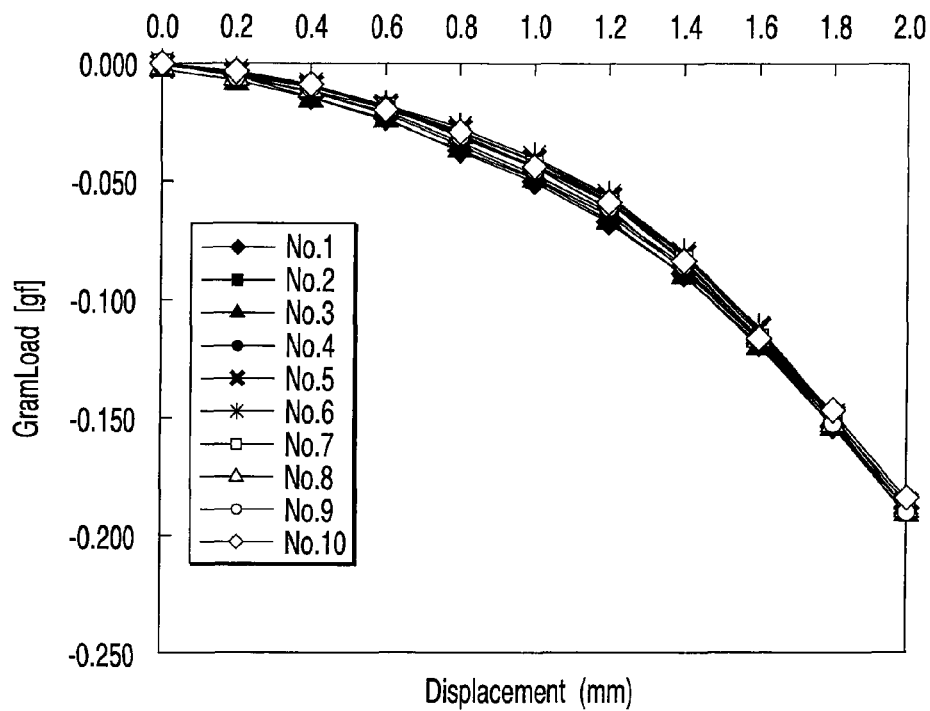
FIG. 12 is a graph showing variation of the specific load value of the leaf spring observed when the load is applied based on manual measurement.
Figure 13:
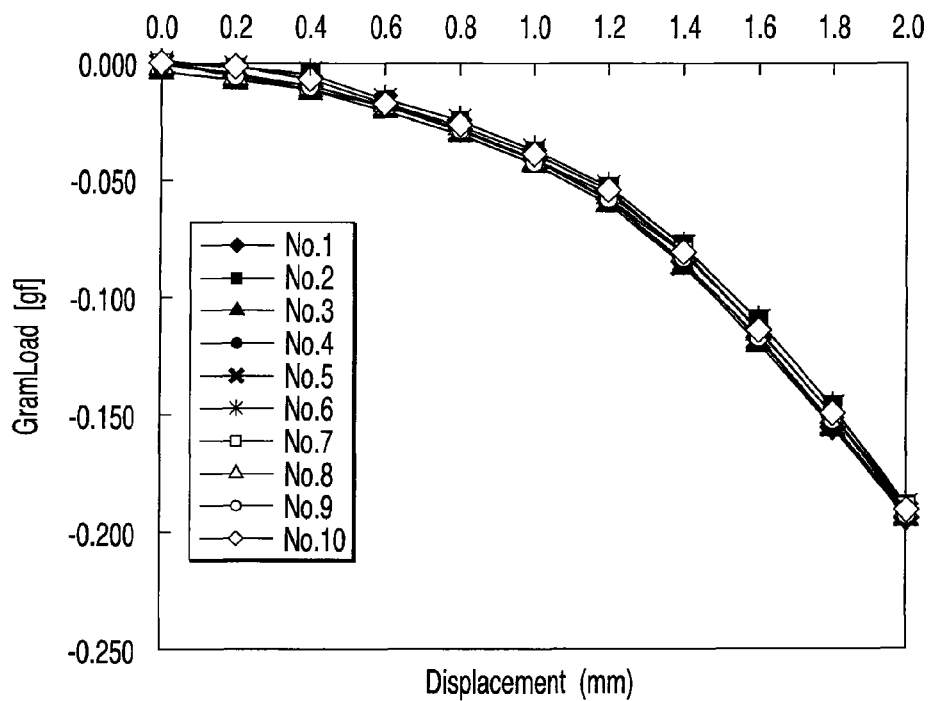
FIG. 13 is a graph showing variation of the specific load value of the leaf spring observed when the load is applied based on automatic measurement.

FIG. 12 is a graph showing variation of the degree of sag of the leaf spring 12 observed when the load is applied with the hold time manually metered. FIG. 13 is a graph showing variation of the degree of sag of the spring 12 observed when the load is applied based on the timer function of the control mechanism 16. In either experiment, the specific load values for 10 samples of the spring 12 are measured. In either of FIGS. 12 and 13, the ordinate and abscissa represent the load (gf) and the displacement (mm) as the backbend, respectively. As shown in FIG. 12, the variation of the degree of sag or the specific load value varies greatly for leaf springs 12 to which loads with displacements of 0.6 to 1.2 mm are manually applied. As shown in FIG. 13, on the other hand, the specific load value varies little for the leaf springs 12 to which loads are applied with the displacements ranging from 0.6 to 1.2 mm based on automatic measurement.

More specifically, the difference between the upper and lower limits of the specific load values varies between 0.008 and 0.012 gf for the leaf springs 12 to which loads are applied with the displacements ranging from 0.6 to 1.2 mm based on manual measurement of the hold time. For the leaf springs 12 to which loads are applied with the displacements ranging from 0.6 to 1.2 mm based on automatic measurement, on the other hand, the difference between the upper and lower limits of the specific load values is restricted to 0.004 to 0.007 gf. While a standard deviation σ of the specific load values obtained by manually measuring the 10 samples is 0.0028, a standard deviation σ of the specific load values obtained by automatically measuring the 10 samples is 0.0023. Thus, the degree of variation of the specific load values is improved by 18% by the timer function of the control mechanism 16.

A flow of measurement of second and subsequent specific load values of the leaf spring 12 will now be described with reference to FIG. 14. The measurement of the second and subsequent specific load values, unlike the measurement of the first load shown in FIG. 6, does not involve Steps S11 for registered coordinate setting, S12 for standby time and hold time input, S13 for set data saving, S16 for standby time and hold time change, S17 for standby time and hold time settlement, and S18 for set data saving. Instead, the set data are read in Step S31. This is done because the set data are only expected to be read in Step S31, since the registered coordinate setting and the like are already performed in the first cycle.

In the measurement of the second and subsequent load values, the specific load values are measured in Step S32 of FIG. 14. These specific load values are measured in the same steps of procedure as those of the flowchart of FIG. 7. In the measurement of the second and subsequent load values, the operator is not asked to determine whether or not to measure the load with the loaded position changed in Step S29 of FIG. 7, unless there is any special change of setting. The measured specific load values are saved as measurement data in Step S33. Thereupon, the measurement of the second and subsequent loads terminates. Thus, since the initial setting is already performed, the measurement of the second and subsequent loads can be automatically performed by the control mechanism 16.

The above is a description of an embodiment of the leaf spring load measuring device 11. According to the load measuring device 11 of the present embodiment, the degree of sag of the leaf spring 12 can be evaluated accurately and efficiently without regard to the operator's skill or experience. Since the hold time during which the spring 12 is kept in the loaded position can be controlled to be a fixed time by the timer function of the control mechanism 16, in particular, variation of the load value caused in the sagged leaf spring 12 can be suppressed. Since the measuring mechanism 13 doubles as the weighing mechanism, moreover, there is no need of providing a separate weighing mechanism, so that load measuring device 11 can be simplified in structure.

In the load measuring device 11, furthermore, the load, frequency of loading, and hold time measured by the measuring mechanism 13 can be freely selected by the control mechanism 16. Thus, the backbend test can be conducted under optimum conditions. The leaf spring 12 of the present embodiment is a suspension that supports the head of the hard disc drive. If the leaf spring 12 provided by the load measuring device 11 has resistance against sag, therefore, it can serve to enhance the durability of the hard disc drive.

The load measuring device 11 comprises the display unit 7 on which the operation screen is displayed. The operation screen has the numerical display area 60 in which the load value and the displacement are displayed, the graph display area 61 in which the graphs indicative of the load value and the displacement are displayed, and the button location area 62 provided with the buttons that are arranged in the order based on the procedure of the load value measurement. In the case where the load measuring device 11 automatically performs the backbend test, therefore, the operator can recognize the load value of the leaf spring 12 and the like as required. Since the buttons are arranged in the order based on the procedure of the load value measurement, moreover, interruption of operation attributable to the operator's entry mistake can be prevented.

The individual programs cause the computer that constitutes the control mechanism 16 to execute the following process routines. Specifically, a load heavier than the working load is applied to the leaf spring 12 by the measuring mechanism 13 to bend the spring 12 in its thickness direction and the bent state is kept for a predetermined hold time. A load within the range of the working load is applied to the spring 12 by the measuring mechanism 13, and the load value then measured by the measuring mechanism 13 and the displacement value metered by the metering mechanism 14 are acquired. The measured load value and the measured displacement value are stored into the RAM 3 of the computer on a time-series basis. The measured load value and the measured displacement value are displayed on the operation screen. Thus, the backbend test is automatically performed so that the degree of sag of the leaf spring 12 can be efficiently evaluated without involving any artificial error. In the backbend test, moreover, the operator can recognize the measured load value and the measured displacement on the operation screen as required, so that he/she can quickly deal with an abnormal measurement, if any. Since the measured load value and the measured displacement value are stored into the RAM 3 of the computer on a time-series basis, in particular, the cause of abnormality, if any, can be investigated with ease.

The individual programs cause the computer that constitutes the control mechanism 16 to execute the following process routines. Specifically, entry of the hold time is accepted through the operation screen, registration of applied load values that exceed the working load of the leaf spring 12 is accepted through the operation screen, and these values are stored into the RAM 3 of the computer. Thus, the hold time and the applied load value can be set freely, so that the backbend test can be conducted under optimum conditions.

For the measurement of the second and subsequent loads, moreover, the control mechanism 16 can automatically measure the loads without asking the operator to make entry. Thus, the sag resistance of the leaf spring 12 can be efficiently evaluated without involving any artificial error.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A computer readable recording medium having a program stored thereon that is executable by a computer connected to a weighing mechanism which applies a load to a leaf spring, a measuring mechanism which measures a value of the load applied by the weighing mechanism, a metering mechanism which meters a displacement of the leaf spring when the load is applied by the weighing mechanism, and a display mechanism on which an operation screen is displayed, the program causing the computer perform a process comprising:
    applying, by the weighing mechanism, a load heavier than a working load to the leaf spring, thereby bending the leaf spring in a thickness direction thereof;
    maintaining, for a predetermined hold time, the state in which the load heavier than the working load is applied to the leaf spring by the weighing mechanism;
    applying a load within a range of the working load to the leaf spring by the weighing mechanism and acquiring a load value then measured by the measuring mechanism and a displacement value then metered by the metering mechanism;
    storing the measured load value and the metered displacement value in a memory section of the computer on a time-series basis; and
    displaying the measured load value and the metered displacement value on the operation screen.

2. A computer readable recording medium having a program stored thereon that is executable by a computer connected to a weighing mechanism which applies a load to a leaf spring, a measuring mechanism which measures a value of the load applied by the weighing mechanism, a metering mechanism which meters a displacement of the leaf spring when the load is applied by the weighing mechanism, and a display mechanism on which an operation screen is displayed, the program causing the computer perform a process comprising:
    accepting entry of a hold time through the operation screen;
    storing, in a memory section of the computer, the hold time input through the operation screen;
    maintaining, for the hold time stored in the memory section, a state in which a load heavier than a working load is applied to the leaf spring by the weighing mechanism;
    applying a load within a range of the working load to the leaf spring by the weighing mechanism and acquiring a load value then measured by the measuring mechanism and the metered displacement value;
    storing the measured load value and the metered displacement value in the memory section on a time-series basis; and
    displaying the measured load value and the metered displacement value on the operation screen.

3. A computer readable recording medium having a program stored thereon that is executable by a computer connected to a weighing mechanism which applies a load to a leaf spring, a measuring mechanism which measures a value of the load applied by the weighing mechanism, a metering mechanism which meters a displacement of the leaf spring when the load is applied by the weighing mechanism, and a display mechanism on which an operation screen is displayed, the program causing the computer perform a process comprising:
    accepting registration of an applied load value that exceeds a working load of the leaf spring through the operation screen;
    storing, in a memory section of the computer, the applied load value registered through the operation screen;
    applying, by the weighing mechanism, a load equivalent to the applied load value stored in the memory section to the leaf spring, thereby bending the leaf spring in a thickness direction thereof;
    maintaining, for a predetermined hold time, a state in which the load equivalent to the applied load value is applied to the leaf spring by the weighing mechanism;
    applying a load within a range of the working load to the leaf spring by the weighing mechanism and acquiring a load value then measured by the measuring mechanism and a displacement value then metered by the metering mechanism;
    storing the measured load value and the metered displacement value in the memory section on a time-series basis; and
    displaying the measured load value and the metered displacement value on the operation screen.

* * * * *